(12) United States Patent
Römisch et al.

(10) Patent No.: US 6,248,365 B1
(45) Date of Patent: Jun. 19, 2001

(54) USE OF COMPLEMENT INHIBITORS FOR THE PREPARATION OF A PHARMACEUTICAL FOR THE PROPHYLAXIS AND THERAPY OF INFLAMMATORY INTESTINAL AND SKIN DISORDERS AS WELL AS PURPURA

(75) Inventors: Jürgen Römisch; Eric-Paul Pâques, both of Marburg; Robert Bartlett, Darmstadt-Arheiligen; Gerhard Dickneite, Marburg, all of (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 08/087,058

(22) Filed: Jul. 7, 1993

(30) Foreign Application Priority Data

Jul. 9, 1992 (DE) .................................. 42 22 534

(51) Int. Cl.[7] .................................................. A61K 35/16
(52) U.S. Cl. .................. 424/530; 514/2; 514/21; 514/8; 424/94.2
(58) Field of Search .................... 514/2, 21, 8; 424/94.2, 424/94, 530

(56) References Cited

U.S. PATENT DOCUMENTS

| | | | | |
|---|---|---|---|---|
| 4,915,945 | * | 4/1990 | Pelzer et al. | 421/101 |
| 4,981,855 | * | 1/1991 | Naka et al. | 514/258 |
| 5,135,916 | * | 8/1992 | Sims et al. | 514/21 |
| 5,157,019 | * | 10/1992 | Glover et al. | 514/12 |
| 5,166,134 | * | 11/1992 | Lezdey et al. | 514/8 |

FOREIGN PATENT DOCUMENTS

| | | |
|---|---|---|
| 0 222 611 | 5/1987 | (EP) . |
| WO 92/10205 | 6/1992 | (WO) . |

OTHER PUBLICATIONS

Kitano et al, Dis Colon Rectum 35(6):560–567 (1992) Abstract BA93:8089.*

* cited by examiner

*Primary Examiner*—Jean C. Witz
(74) *Attorney, Agent, or Firm*—Finnegan, Henderson, Farabow, Garrett and Dunner, L.L.P.

(57) ABSTRACT

The invention relates to the use of complement inhibitors, especially of C1 inactivator or of factors I or H, for the preparation of a pharmaceutical and for the prophylaxis and therapy of chronic inflammatory intestinal disorders, inflammatory skin disorders and purpura.

6 Claims, No Drawings

USE OF COMPLEMENT INHIBITORS FOR THE PREPARATION OF A PHARMACEUTICAL FOR THE PROPHYLAXIS AND THERAPY OF INFLAMMATORY INTESTINAL AND SKIN DISORDERS AS WELL AS PURPURA

The invention relates to the use of complement inhibitors, especially of C1 inactivator or of factors I or H, for the preparation of a pharmaceutical for the prophylaxis and therapy of chronic inflammatory intestinal disorders, inflammatory skin disorders and purpura.

The complement system is composed of a number of proteins, most of them proteases, which after initial activation lead to the formation of the terminal lysis complex and thus to the destruction of target cells. Such processes are initiated "classically" by formation of immune complexes or contact activation and "alternatively" by exogenous structures such as bacteria and their lipopolysaccharides. The two activation pathways merge in the production of component C3b which, together with C5–C9, initiates the membrane attack complex. Proteolytic activation of components C3, C4 and C5 leads to release of the anaphylatoxins C3a, C4a and C5a, which have chemotactic effects on inflammatory cells.

The principal physiological regulators of the complement system are the proteins which have inhibitory activity—C1 inactivator, factor I (also called C3b inactivator) and its accelerator factor H. The first-mentioned inhibitor displays its effect at the site of initiation of the "classical" pathway by interaction with the activating protease. By contrast, factor I is a protease whose catalytic action is considerably increased by factor H and which inactivates the C3b molecule as well as the C4b molecule by partial degradation and thus intervenes in a regulatory/inhibitory manner at the merging of the "classical" and "alternative" pathway.

Activation of the complement system has been observed during the course of a number of autoimmune diseases, including lupus erythematosus and rheumatoid arthritis. These activation processes are generally associated with a consumption of the factors involved, especially of the inhibitors. Although an increase in the complement factors may often be observed during the course of the acute phase reaction, the inhibitory capacity is insufficient to control complement activation and the consequences resulting therefrom. Replacement of these regulators or prophylactic administration therefore appears worthwhile. The therapeutic value of factors I and H for glomerulonephritis has been described in EP-A-0 222 611.

The etiopathogenesis of chronic inflammatory intestinal disorders, especially "Crohn's disease" and "ulcerative colitis" has not been explained to date. A "primary stimulus" initiates an immune process which is followed by tissue infiltration of inflammatory cells and finally damage to cells and tissues. The clinical signs are ulcers, fistulations and frequent hemorrhagic stools/diarrhoea, which are associated with attacks of fever and spasmodic pain.

It has not to date been possible to define for these disorders pathognomonic autoantibodies or autoreactive T cells which identify such inflammatory processes as autoimmune disease. Involvement of immune processes which may result in complement activation is not ruled out, however. It is moreover possible for the resulting anaphylatoxins C3a, C4a and C5a to contribute to attracting inflammatory cells. Also noteworthy are the edemas of the intestinal mucosa which occur in the early phase of the disorder and are typically observed after activation of the complement system.

Elevated C5a levels are also measured in skin disorders such as, for example, in pustular dermatoses, dermatitides or psoriasis and unambiguously prove the activation of the complement system and mediate the attraction of inflammatory cells. The latter in turn make a crucial contribution to the severity of the clinical picture.

It is also possible in the clinical picture of purpura for, for example, endothelial cells to be subject to edematous changes leading to capillary dilatation. The clinical manifestation of this condition is erythema/edema, for example, at the site of the cutaneous lesion. The term "purpura" is generally understood to mean the extravasation of "formed elements of the blood" from dermal blood vessels into the skin (for example dermis). In idiopathic thrombocytopenic purpura there is typically a tendency to bleed with hematoma formation (extravasation), which is crucially assisted by a depletion of blood platelets. An "inflammatory" purpura is frequently associated with vasculitis which may be caused by immune complexes.

Accordingly, chronic inflammatory intestinal disorders as well as purpura (associated with dermal necroses) and inflammatory skin disorders have the extravasation of fluid (from blood vessels) in common. The formation of edema which frequently results, as well as the attraction and infiltration of inflammatory cells into the inflammatory tissue are processes which are frequently observed after activation of the complement system.

The animal model known as the "Arthus reaction" is frequently used for investigation of the described processes and for the pharmacological testing of therapeutically active substances (see Example 1).

We have now found that the complement inhibitors C1 inactivator and the factors I and H have an inhibitory effect on the Arthus reaction.

It is accordingly possible to use complement inhibitors, especially C1 inactivator and/or factor I and/or factor H-containing solutions, for the prophylaxis and therapy of inflammatory skin disorders such as, for example, pustular dermatoses, dermatitides or psoriasis and intestinal disorders, especially Crohn's disease and ulcerative colitis, as well as inflammatory purpura (associated with dermal necroses).

The invention relates to the use of complement inhibitors for the preparation of a pharmaceutical for the prophylaxis and therapy of chronic inflammatory intestinal disorders, inflammatory skin disorders and purpura. The C1 inactivator and the factors I and H or combinations of these are particularly suitable.

Purified inhibitors, which can be prepared from blood plasma in a manner known to the person skilled in the art, are preferably used.

Inhibitors expressed by genetic engineering means and purified can also be used for this purpose.

The dosages used on administration by the intravenous (bolus or infusion), intramuscular or subcutaneous route are as follows:

C1 inactivator: 1–5000 IU/kg body weight (BW) per day, preferably 5–500 IU/kg×day.

Factor I: 0.005–100 mg/kg BW per day, preferably 0.01–50 mg/kg×day.

Factor H: 0.005–100 mg/kg BW per day, preferably 0.01–50 mg/kg×day.

The inhibitors can be used separately or in combination. In general, administration of only one of these inhibitors is sufficient.

A combination of the inhibitory proteins appears worthwhile especially when the activation of two complement pathways, the classical and the alternative, cannot be ruled out. Although C1 inactivator alone inhibits contact activation of the classical pathway and thus also the subsequent release of the anaphylatoxins, it has no effect on the alternative pathway. By contrast, production of the terminal lysis complex can be controlled by the use of factors I and/or H. Consumption of the complement factors up to the point of merging of the two activation pathways cannot, by contrast, be stopped by use of factors I and H alone.

EXAMPLE

The Arthus reaction, identified as acute, necrotizing, inflammatory lesion of blood vessels, is induced by immunization and subsequent challenge with an exogenous antigen or directly with an antibody directed against the test species. Extravasation, formation of edema and attraction of inflammatory cells characterize the Arthus reaction. The parameter measured is the extent of the formation of edema in the rear paw of a rat. The better the reduction/prevention of this formation of edema, the more effective is the substance tested as therapeutic agent.

The results of the investigation of the complement inhibitors on the Arthus reaction are listed in Table 1. Both C1 inactivator and factor H as well as factor I have an inhibitory effect on the formation of edema after administration of an i.v. bolus. Factor I significantly prevents swelling on subcutaneous administration too.

Table 1: Effect of C1 inactivator, factor I and factor H on the Arthus reaction in the rat paw The inhibition (%) of swelling was determined by comparison with a control group (placebo). A group was treated with prednisolone as positive control. The test substances were administered one hour before challenge (i.v.= intravenous; s.c.=subcutaneous; p.o.=oral), and the swelling of the paw was measured four hours thereafter (10 animals/group).

| Substance | Dose | Administration | Inhibition (%) |
|---|---|---|---|
| C1 inactivator | 100 IU/kg | i.v. | 12 |
|  | 200 IU/kg | i.v. | 38 |
| Factor I | 0.05 mg/kg | i.v. | 43 |
|  | 0.50 mg/kg | i.v. | 55 |
|  | 5.00 mg/kg | i.v. | 65 |
|  | 10.00 mg/kg | s.c. | 59 |
|  | 20.00 mg/kg | s.c. | 57 |
| Factor H | 1.0 mg/kg | i.v. | 35 |
|  | 10.0 mg/kg | i.v. | 44 |
| Prednisolone | 29.0 mg/kg | p.o. | 70 |

What is claimed is:

1. A method for the treatment of inflammatory skin disorders, intestinal disorders or purpura which method comprises administering one or more complement inhibitors from the group consisting of C1 inactivator, factor I and factor H.

2. A method as claimed in claim 1, for the treatment of Crohn's disease or ulcerative colitis.

3. A method as claimed in claim 1, for the treatment of pustular dermatoses, dermatitis or psoriasis.

4. A method as claimed in claim 1, which comprises administering 1–5000 IU/kg×day C1 inactivator, 0.005–100 mg/kg×day factor I, or 0.005–100 mg/kg×day factor H.

5. A method as claimed in claim 1, which comprises administering 5–500 IU/kg×day C1 inactivator, 0.01–50 mg/kg×day factor I, or 0.01–50 mg/kg×day factor H.

6. A method as claimed in claim 1, wherein the complement inhibitor is administered intravenously, intramuscularly or subcutaneously.

* * * * *